United States Patent [19]

Homeier

[11] 4,039,585

[45] Aug. 2, 1977

[54] HYDROFORMYLATION PROCESS

[75] Inventor: Edwin H. Homeier, Maywood, Ill.

[73] Assignee: UOP Inc., Des Plaines, Ill.

[21] Appl. No.: 611,471

[22] Filed: Sept. 8, 1975

[51] Int. Cl.$^2$ .................. C07C 45/02; C07C 45/08
[52] U.S. Cl. .................. 260/604 HF; 260/632 HF
[58] Field of Search .................. 260/604 HF, 632 HF

[56]  References Cited

U.S. PATENT DOCUMENTS

| 2,526,742 | 10/1950 | Gresham et al. | 260/586 R |
|---|---|---|---|
| 2,648,694 | 8/1953 | Mason | 260/604 HF |
| 2,945,050 | 7/1960 | Franke | 260/604 HF |
| 3,725,305 | 4/1973 | Wilkinson | 260/604 HF |

OTHER PUBLICATIONS

Kundo et al., "Chem. Abstract", vol. 69, (1968), p. 67677u.

*Primary Examiner*—James O. Thomas, Jr.
*Assistant Examiner*—W. B. Lone
*Attorney, Agent, or Firm*—James R. Hoatson, Jr.; Kimbley L. Muller; William H. Page, II

[57]  ABSTRACT

A hydroformylation process is disclosed which comprises hydroformylating an olefinic compound possessing an alpha olefinic double bond with carbon monoxide and hydrogen in the presence of a catalyst system comprising a Group IB metal phthalocyanine compound or said compound dispersed on a solid support.

18 Claims, No Drawings

HYDROFORMYLATION PROCESS

This invention relates to the hydroformylation of an olefinic compound. More specifically, this invention relates to a process for the preparation of hydroformylation products which comprises hydroformylating an olefinic compound possessing an alpha olefinic double bond with carbon monoxide and hydrogen in the presence of a catalyst system comprising a Group IB metal phthalocyanine compound.

It is well known in the art that hydroformylation products comprising substantial amounts of alcohols and aldehydes may be formed by the hydroformylation of an unsaturated compound with carbon monoxide and hydrogen in the presence of certain catalytic compositions of matter. The resultant hydroformylation products correspond to compounds which are obtained by the addition of a carbonyl or carbinol group to an olefinically unsaturated carbon atom in the starting material or some double bond-isomerized derivative thereof with simultaneous saturation of the olefinic bond. The general process known as hydroformylation involves a reaction which may be shown by the general generic formula:

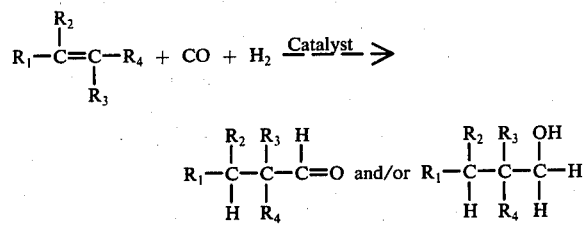

wherein $R_1$, $R_2$, $R_3$ and $R_4$ may be chosen from a group comprising an organic, halide or hydrogen radical.

It has been shown in the prior art that dicobalt octacarbonyl has generally been used as a catalyst for the hydroformylation of unsaturated compounds. This catalyst, which can be prepared from many forms of cobalt, usually decomposes rapidly at elevated temperatures unless high pressures of about 100–4500 pounds per square inch gauge of carbon monoxide are maintained, depending on the temperature. Another serious disadvantage of hydroformylation processes has been the necessity of proceeding in two steps when alcohols are the desired products. Another disadvantage inherent in the hydroformylation process is the relative inability to direct the reactions involved to the production of predominantly terminal alcohols when the olefins contain more than 3 carbon atoms, particularly when the charge stock to the process comprises a mixture of internal and terminal (alpha) olefinic bonds. Yet another disadvantage in the hydroformylation processes known to the prior art is the problem of metal recovery in a homogeneous catalyst system.

In contradistinction to the prior art, it has now been found that the utilization of a catalyst system comprising a Group IB metal phthalocyanine compound during the hydroformylation of an olefinic compound possessing an alpha olefinic bond by carbon monoxide and hydrogen will add a different dimension to the hereinbefore set forth basic hydroformylation process. The utilization of the present invention will allow the manufacturer of various alcohols and aldehydes a selective process whereby only terminal olefins will be hydroformylated from a charge stock comprising both internal and terminal olefinic compounds. The process of this invention will also allow for a continual and more feasible method of catalyst recovery as a result of the ease of removing the heterogeneous catalyst which is present when the Group IB metal phthalocyanine compound is dispersed on a solid support. The advantage of the recovery of the heterogeneous metal catalyst system without great expenditure of money will result in a less expensive production of the alcohols and aldehydes as a result of the amortization of the total cost of the process over a long period of time.

The desired products of the process of this invention, namely alcohols and aldehydes, are utilized in the chemical industry in many ways. For example, alcohols are utilized in the synthesis of other organic derivatives; as solvents; as an extraction medium; in dyes; synthetic drugs; synthetic rubber; detergents; cleaning solutions; surface coatings; cosmetics; pharmaceuticals; in the preparation of esters; as a solvent for resin in coatings; as a plasticizer; dyeing assistant; hydraulic fluids; detergent formulations; dehydrating agents; or the use of aldehydes as exemplified by their utility as perfumeries or in the synthesis of primary alcohols.

It is therefore an object of this invention to provide a novel process for the preparation of alcohols and aldehydes.

A further object of this invention is to provide an improvement in the process for the preparation of hydroformylation products utilizing certain catalytic compositions of matter which will permit the recovery of the desired hydroformylation compounds and catalytic compositions of matter in a more economically feasible manner.

In one aspect an embodiment of this invention resides in a process for the preparation of hydroformylation products which comprises the hydroformylation of an olefinic compound possessing an alpha olefinic double bond with carbon monoxide and hydrogen at hydroformylation condition in the presence of a catalyst system comprising a Group IB metal phthalocyanine compound and recovering the resultant hydroformylated products.

Another aspect of this invention resides in a process for the preparation of hydroformylation products which comprises the hydroformylation of an olefinic compound possessing an alpha olefinic double bond with carbon monoxide and hydrogen at hydroformylation conditions in the presence of a heterogeneous catalyst system comprising a Group IB metal phthalocyanine compound dispersed on a solid support, and recovering the resultant hydroformylated products.

A specific embodiment of this invention resides in a process for preparing butyraldehyde which comprises hydroformylating propylene with carbon monoxide and hydrogen in the presence of a catalyst system comprising a copper phthalocyanine at a temperature of 115° C. and a pressure of 100 atmospheres of hydrogen and 100 atmospheres of carbon monoxide, said catalytic component comprising 0.01 mols of copper phthalocyanine per mol of propylene, and recovering the resultant butyraldehyde.

Another specific embodiment of this invention resides in a process for preparing 3-methylhexanol-1 by the hydroformylation of 2-methylpentene-1 in the presence of a copper phthalocyanine compound dispersed on a lignite-derived charcoal at a temperature of 100° C. and a pressure of 100 atmospheres of hydrogen and 100 atmospheres of carbon monoxide and recovering the resultant 3-methylhexanol-1.

Other objects and embodiments will be found in the following further detailed description of the present invention.

As hereinbefore set forth the present invention is concerned with a process for preparing hydroformylated products, namely, alcohols and aldehydes, said process being effected by the hydroformylation of an olefinic compound possessing an alpha olefinic double bond with carbon monoxide and hydrogen in the presence of a catalyst system comprising a Group IB metal phthalocyanine compound or a Group IB metal phthalocyanine compound dispersed on a solid support. The reaction is effected under hydroformylation conditions which include a temperature in the range of from about 15° C. to about 300° C. and preferably in a range of from about 60° C. to about 200° C. In addition, another reaction condition involves pressures, said pressures ranging from about atmospheric up to 500 atmospheres or more. The superatmospheric pressures which are employed are afforded by the introduction of gaseous carbon monoxide, hydrogen and, if desired, any substantially inert gas such as nitrogen or helium may also be charged to the hydroformylation zone. Another reaction variable which is employed is the proportional amount of components of the catalyst system present in the hydroformylation process. It is contemplated within the scope of this invention that the heterogeneous catalyst system comprising a metal phthalocyanine compound or said compound dispersed on a solid support will be present in a molar ratio of from about 0.00001 mols of the metal catalyst phthalocyanine compound to about 10.0 mols of the metal catalyst phthalocyanine compound per mol of the unsaturated compound.

Examples of suitable olefinic compounds possessing an alpha olefinic bond which are utilized as the starting material in the hydroformylation process of this invention include, in particular, olefinic compounds possessing from 3 to 30 carbon atoms, alkyl, carbonyl, carbonyloxy, hydroxy, carboxyl, oxy, amide, amine, nitrile, dienic, or halo-substituted olefinic compounds possessing from about 3 to about 30 carbon atoms, cycloolefinic hydrocarbon possessing from about 5 to about 10 carbon atoms such as propylene, butene-1, isobutene, pentene-1, 2-methylbutene-1, hexene-1, 3-methylpentene-1, heptene-1, octene-1, 3-methylheptene-1, decene-1, undecene-1, pentadecene-1, nonene-1, undecene-1, dodecene-1, tridecene-1, tetradecene-1, 2-methoxybutene-1, 2-methoxypentene-1, 2-ethoxyhexene-1, 1-propoxyheptene-1, 2-ethoxyoctene-1, hexadecene-1, heptadecene-1, octadecene-1, nonadecene-1, eicosene-1, heneicosene-1, docosene-1, tricosene-1, tetracosene-1, pentacosene-1, hexacosene-1, heptacosene-1, octacosene-1, nonacosene-1, tricontene-1, cyclopentene, cyclohexene, cycloheptene, cyclooctene, cyclononene, cyclodecene, 1-methylcyclohexene-1, 1-ethylcyclohexene-1, 2,3-dipropylcycloheptene-1, 1-methoxycylopentene-1, 2,3-dipropylcycloheptene-1, 1-chlorocycloheptene-1, 2,3,4-trichlorocyclooctene-1, hex-1-ene-5-one, oct-1-ene-6-one, non-1-ene-6-one, dec-1-ene-3-one, dodec-1-ene-6-one, tridec-1-ene-5-one, tetradec-1-ene-2-one, pentadec-1-ene-5-one, hexadec-1-ene-5-one, eicos-1-ene-5-one, pentacos-1-ene-11-one, 1-butenyl acetate, 1-pentenyl acetate, 1-heptenyl acetate, 1-octenyl acetate, 1-nonenyl acetate, 1-undecenyl acetate, 1-tetradecenyl acetate, 1-hexadecenyl acetate, 1-heneicosenyl acetate, but-1-ene-3-ol, pent-1-ene-3-ol, hex-1-ene-4-ol, hept-1-ene-3-ol, oct-1-ene-3-ol, non-1-ene-4-ol, dec-1-ene-4-ol, undec-1-ene-4-ol, dodec-1-ene-4-ol, tridec-1-ene-6-ol, tetradec-1-ene-6-ol, eicos-1-ene-6-ol, tetracos-1-ene-8-ol, pentacos-1-ene-7-ol, tricont-1-ene-23-ol, 1-butenoic acid, 1-pentenoic acid, 1-hexeneoic acid, 1-hepteneoic acid, 1-octeneoic acid, 1-deceneoic acid, 1-nonacoseneoic acid, 1-triaconteneoic acid, 2-methoxybut-1-ene, 2-ethoxyoct-1-ene, 4-ethoxyheptadec-1-ene, 1,3-dimethoxy-12-ethoxy-5,6-dipropoxytricont-1-ene, 1-buteneamide, 1-penteneamide, 1-hexeneamide, 1-hepteneamide, 1-dodeceneamide, 1-trideceneamide, 1-tetradeceneamide, 1-heptadeceneamide, 1-octadeceneamide, 1-nonadeceneamide, 1-eicoseneamide, 1-heneicoseneamide, 1-docoseneamide, 1-tricoseneamide, 1-tetracoseneamide, 1-pentacoseneamide, 1-hexacoseneamide, 1-heptacoseneamide, 1-octacoseneamide, 1-nonacoseneamide, 1-triconteneamide, 1-buteneamine, 1-penteneamine, 1-hexeneamine, 1-hepteneamine, 1-octeneamine, 1-noneneamine, 1-deceneamine, 1-undeceneamine, 1-dodeceneamine, 1-trideceneamine, 1-tetradeceneamine, 1-hexadeceneamine, 1-heptadeceneamine, 1-octadeceneamine, 1-nonadeceneamine, 1-eicoseneamine, 1-heneicoseneamine, 1-docoseneamine, 1-tricoseneamine, 1-tetracoseneamine, 1-pentacoseneamine, 1-hexacoseneamine, 1-heptacoseneamine, 1-octacoseneamine, 1-nonacoseneamine, 1-triconteneamine, 1-butenenitrile, 1-pentenenitrile, 1-heptenenitrile, 1-hexenenitrile, 1-octenenitrile, 1-nonenenitrile, 1-decenenitrile, 1-undecenenitrile, 1-tridecenenitrile, 1-tetradecenenitrile, 1-pentadecenenitrile, 1-hexadecenenitrile, 1-heptadecenenitrile, 1-octadecenenitrile, 1-nonadecenenitrile, 1-eicosenenitrile, 1-heneicosenenitrile, 1-docosenenitrile, 1-tricosenenitrile, 1-tetracosenenitrile, 1-pentacosenenitrile, 1-hexacosenenitrile, 1-heptacosenenitrile, 1-octacosenenitrile, 1-nonacosenenitrile, 1-tricontenenitrile, 1-chlorobutene-1, 2-chloropentene-1, 2-bromohexene-1, 2,3-dichlorooctene-1, 3-iodooctene-1, 2-methoxy-3-chlorodecene-1, 3,4-dimethyl-2-chlorooctene-1, etc.

It is also contemplated within the scope of this invention that the alpha olefinic compound may be present in a mixture with internal olefinic compounds such as a mixture of decene-1 and decene-5 or tetradecene-7, decene-5 and tetradecene-1, where the alpha olefinic compound will be hydroformylated by the carbon monoxide and hydrogen in contrast to the internal olefinically-bonded compounds which will remain inert to the hydroformylation reactants. It is also contemplated that the process of this invention may be operated as a separation process for the obtention of substantially pure internal olefins from a mixture of internal and terminal olefins by hydroformylation of alpha olefins and the recovery of the relative inert internal olefins from the resultant hydroformylated products derived for the carbinol or carbonyl addition to the alpha olefinic bond. The mixture of internal and terminal olefinic compounds will include mixtures of linear internal and alpha olefinic compounds such as internal olefinic compounds possessing carbon numbers of 8 through 10, 11 through 14 or 15 through 18, etc., where the terminal or alpha olefinic compounds are the only reactants hydroformylated in the presence of the catalyst system of the present invention. It is also contemplated within the scope of this invention that the alpha olefinic compound may also contain an internal double bond such as 1,5-pentadiene, 1,7-tetradecadiene, 1,5-decadiene, 1,4-hexadiene, 1,7-octadiene, 1,6-pentacosadiene, 1,5-tricontadiene, etc., to produce alcohols and aldehydes possessing the internal double bond.

It is contemplated within the scope of the process of the present invention that the hydroformylation reaction may be effected in an inert reaction medium. The inert reaction medium may be both organic or inorganic in nature such as an aqueous reaction medium such as water, an alkaline reaction medium such as sodium hydroxide or a basic reaction medium such as ammonia. The reaction medium may also be organic in nature as exemplified by n-pentane, n-hexane, n-heptane, n-octane, n-nonane, isooctane (2,2,4-trimethylpentane), cyclohexane, methylcyclohexane, benzene, toluene, etc. In a preferred embodiment of this invention the hydroformylated medium may be charged to the metal phthalocyanine solid support continuously or intermittently as economic conditions necessitate.

The catalytic composition of the present invention comprises a catalyst system comprising a Group IB metal phthalocyanine compound or a heterogeneous system comprising a Group IB metal phthalocyanine dispersed on a solid support. The Group IB metal phthalocyanine compound will comprise any phthalocyanine compound containing copper, silver or gold or any combination thereof. Suitable Group IB metal phthalocyanine compounds may be exemplified by copper phthalocyanine monosulfonate, copper phthalocyanine disulfonate, copper phthalocyanine trisulfonate, copper phthalocyanine tetrasulfonate, silver phthalocyanine monosulfonate, silver phthalocyanine disulfonate, silver phthalocyanine trisulfonate, silver phthalocyanine tetrasulfonate, gold phthalocyanine monosulfonate, gold phthalocyanine disulfonate, gold phthalocyanine trisulfonate, gold phthalocyanine tetrasulfonate, copper phthalocyaninecarboxylate, copper phthalocyaninedicarboxylate, copper phthalocyaninetricarboxylate, copper phthalocyaninetetracarboxylate, silver phthalocyaninecarboxylate, silver phthalocyaninedicarboxylate, silver phthalocyaninetricarboxylate, silver phthalocyaninetetracarboxylate, gold phthalocyaninecarboxylate, gold phthalocyaninedicarboxylate, gold phthalocyaninetricarboxylate, gold phthalocyaninetetracarboxylate, copper aminophthalocyanine, copper diaminophthalocyanine, copper triaminophthalocyanine, copper tetraaminophthalocyanine, silver aminophthalocyanine, silver diaminophthalocyanine, silver triaminophthalocyanine, silver tetraaminophthalocyanine, gold aminophthalocyanine, gold diaminophthalocyanine, gold triaminophthalocyanine, gold tetraaminophthalocyanine, copper nitrophthalocyanine, copper dinitrophthalocyanine, copper trinitrophthalocyanine, copper tetranitrophthalocyanine, silver nitrophthalocyanine, silver dinitrophthalocyanine, silver trinitrophthalocyanine, silver tetranitrophthalocyanine, gold nitrophthalocyanine, gold dinitrophthalocyanine, gold trinitrophthalocyanine, gold tetranitrophthalocyanine, copper chlorophthalocyanine, copper dichlorophthalocyanine, copper trichlorophthalocyanine, copper tetrachlorophthalocyanine, silver chlorophthalocyanine, silver dichlorophthalocyanine, silver trichlorophthalocyanine, silver tetrachlorophthalocyanine, gold chlorophthalocyanine, gold dichlorophthalocyanine, gold trichlorophthalocyanine, gold tetrachlorophthalocyanine, copper hydroxyphthalocyanine, copper dihydroxyphthalocyanine, copper trihydroxyphthalocyanine, copper tetrahydroxyphthalocyanine, silver hydroxyphthalocyanine, silver dihydroxyphthalocyanine, silver trihydroxyphthalocyanine, silver tetrahydroxyphthalocyanine, gold hydroxyphthalocyanine, gold dihydroxyphthalocyanine, gold trihydroxyphthalocyanine, gold tetrahydroxyphthalocyanine. As hereinbefore set forth, the Group IB metal phthalocyanine catalytic composition of matter may be present in a range of from about 0.00001 mols of the Group IB metal phthalocyanine catalyst to about 10.0 mols of the Group IB metal phthalocyanine catalyst per mol of the olefinic compound possessing an alpha double bonded carbon atom which is hydroformylated to the resultant alcohol or aldehyde. In manufacturing the various Group IB phthalocyanine compounds which may be impregnated on a solid support, it is contemplated that any impregnation or dispersal technique known to the art may be utilized in the forming of the solid support catalyst system. It is contemplated that various ligands may be present in the final catalytic composition of matter such as fluoride, bromide, iodide, phosphorus, phosphines, phosphates, sulfates, arsenates, antimony, nitrates, perchlorates, etc. It is also contemplated that the Group IB metal phthalocyanine may be present in a liquid-liquid system for olefinic contact in an interface of the liquid-liquid system. The solid support of the present invention will comprise any solid support such as $\alpha$-, $\beta$-, $\gamma$-alumina, silica, silica-alumina mixtures, pumice, lignite-derived charcoal, bituminous-derived charcoal, charcoal which is derived from vegetable sources such as wood pulp, charcoal which is extradited from petroleum black, bone char charcoal, thallia, zirconia, mordenite, faujasite, stillbite, thomsonite, magnesia, analcite, chabazite, heulandite, natrolite, various clays, kieselguhr, ion exchange resins such as sulfonic acid resins, carboxylic acid resins, phenolic resins or aminoresins, etc.

It is understood that the aforementioned olefinic compounds possessing alpha olefinic bonding, inert reaction mediums, Group IB metal phthalocyanine compounds, catalytic ligands and solid supports are only representative of the type of compounds which may be employed in the present invention and that the present invention is not necessarily limited thereto.

The process of this invention may be effected in any suitable manner and may comprise either a batch or continuous type operation. For example, when a batch type operation is employed, the reactants comprising the olefinic compound possessing an alpha olefinic carbon bond, carbon monoxide and hydrogen are placed in an appropriate apparatus along with a Group IB metal phthalocyanine or a Group IB metal phthalocyanine dispersed on a solid support. The autoclave is sealed, heated to a desired operating temperature and maintained thereat for a predetermined residence time. At the end of this time which may range from 0.5 up to 50 hours or more in duration, the heating is discontinued, the autoclave is allowed to return to room temperature and the autoclave is vented thereby allowing it to return to ambient pressure. The reaction mixture is then recovered, separated from the catalyst system by catalyst recovery methods known to the art and subjected to conventional means of purification and separation, said means including washing, drying, extraction, evaporation, fractional distillation, etc., whereby the desired hydroformylation products, namely terminal alcohols and aldehydes or terminal alcohol-terminal aldehyde mixtures, are recovered from the reaction mixture.

It is also contemplated within the scope of this invention that the hydroformylation process for obtaining the desired alcohols and adehydes will be effected in a continuous manner of operation. When such a type of operation is employed, the reactants comprising the olefinic compound possessing an alpha olefinic double bond in the terminal position are continuously charged to the hydroformylation zone containing the catalyst system of the present invention comprising a Group IB metal phthalocyanine compound dissolved in the reaction medium or a heterogeneous catalyst system comprising a Group IB metal phthalocyanine compound dispersed on a solid support. The hydroformylation zone is maintained at proper operating conditions of pressure and temperature by heat and the admission of requisite amounts of carbon monoxide and hydrogen and any substantially inert gas desired for effecting the hydroformylation reaction. After completion of the desired residence time, the reactor effluent is continuously withdrawn and subjected to conventional means of separation whereby the desired terminal alcohols, terminal aldehydes, or terminal aldehyde-terminal alcohol mixtures are recovered while any unreacted starting material comprising the olefinic compound possessing an alpha olefinic double bond, olefinic compounds possessing internal double bonds, carbon monoxide and hydrogen are recycled to the reaction zone to form a portion of the feed stock or gaseous hydrogen or carbon monoxide stream.

Examples of alcohols and aldehydes which may be prepared according to the process of this invention will include butanol-1, pentanol-1, 3-n-propylpentanol-1, hexanol-1, heptanol-1, octanol-1, nonanol-1, decanol-1, 2-methylbutanol-1, 2-methylpentanol-1, 2-ethylpentanol-1, 2-methylhexanol-1, 2-ethylhexanol-1, 2-chloropropanol-1, 3-chlorohexanol-1, 2,3-dichloroheptanol-1, 2-ethyl-3-chlorooctanol-1, terminal butanal, terminal butyraldehydes, terminal pentanals, terminal hexanals, terminal heptanals, 2-n-butylheptanal, terminal octanals, terminal nonanals, terminal decanals, 2-n-amyldecanal-1, terminal undecanals, 2-methylbutanal-1, 2-methyloctanal-1, cyclopentyl carbinol, cyclohexyl carbinol, cycloheptyl carbinol, cyclooctyl carbinol, cyclononyl carbinol, cyclodecyl carbinol, 2-methyl-6-octanone-1-al, 2-ethyl-6-octanone-1-al, 1-formyleicosyl acetate, 1-formylhexadecyl acetate, 2-methyl-5-octanol-1-al, 2-ethyl-7-tetradecanol-1-al, 2-methyl-6-undecanol-1-al, 1-formyl octanoic acid, 1-formyl tetradecanoic acid, 1-formyl pentacosanoic acid, 1-formyl hexadecanoic acid, formyl nonanoic acid, 6-methoxytridecanal-1, 4-ethoxytetradecanal-1, 3-exthoxypentacosanal-1, 4-propoxyhexadecanal-1, 3-methoxynonanal-1, 1-formyl hexanamide, 1-formyl tetradecanamide, 1-formylundecylamine, 1-formyltetradecylamine, 1-formylpentacosylamine, 1-formylbutanenitrile, 1-formyltetradecanenitrile, 1-formyltetracosanenitrile, mixed hydroxymethylalkanes, mixed formylalkanes, etc.

The following examples are given to illustrate the process of the present invention which, however, are not intended to limit the generally broad scope of the present invention in strict accordance therewith.

EXAMPLE I

In this example copper 4-bromophthalocyanine was tested as a heterogeneous hydroformylation catalyst in the presence of both an internal and an alpha olefin. A glass-lined, 300 ml, stainless-steel, rocking autoclave which was equipped with external heating and temperature regulation devices was charged with 2.0 grams (3.0 mmols) of the copper 4-bromophthalocyanine and 12 grams (85.6 mmols) of decene-5 (Phillips Technical Grade.) After the autoclave was sealed and flushed with nitrogen 12 grams (285 mmols) of propylene (Matheson Technical Grade) was charged to the autoclave in a liquid form by means of a pressurized liquid charging apparatus. The autoclave was then pressurized to an initial pressure of 100 atmospheres of carbon monoxide and an additional 100 atmospheres of hydrogen. The autoclave was then heated to 115° C. for 18 hours, after which it was cooled to room temperature and the excess gas pressure was carefully vented to a hood. The autoclave was flushed with nitrogen to remove residual carbon monoxide and hydrogen and the liquid product was recovered and analyzed by standard gas-liquid chromatography procedures. The analysis disclosed that 20 mmols of the propylene (9.8 mol % yield base on the propylene charged) had been converted to butyraldehydes (about 45% normal butyraldehyde) while the decene-5 was recovered unchanged.

The copper 4-bromophthalocyanine was recovered as an insoluble solid from the product mixture and reused in Example II below.

These results first of all demonstrate the high selectivity achieved on using copper 4-bromophthalocyanine as a catalyst, since the internal olefin, decene-5, was recovered unchanged from the reaction mixture while the terminal olefin, propylene, was converted to the corresponding aldehyde. Furthermore, the heterogeneous nature of the catalyst is clearly shown in this experiment, since the insoluble phthalocyanine complex was recovered from the product mixture by the simple procedure of decanting the product from the catalyst. The ease with which the catalyst and products were separated demonstrates a substantial improvement over the expensive and time-consuming catalyst recovery methods presently required in the hydroformylation of olefins by homogeneous catalysts known in the art.

EXAMPLE II

In this example the catalyst recovered from Example I was used to hydroformylate a terminal olefin in the absence of an internal olefin. The recovered catalyst of Example I was charged in the same fashion as described in Example I to the 300 ml autoclave along wth 23 grams of n-heptane as a solvent. After the autoclave was flushed with nitrogen, 12 grams of propylene was charged as before and the autoclave was pressurized to 100 atmospheres each of carbon monoxide and hydrogen. The autoclave was heated to 120° C. for 18 hours, cooled, depressurized and flushed as set forth in Example I. An analysis of the liquid product by standard gas-liquid chromatographic techniques disclosed that 38 mmols of the propylene (13.2 mol % yield based on propylene charged) had been converted to butyraldehydes (approximately 50% normal butyraldehyde).

This example demonstrates that the recovered heterogeneous copper phthalocyanine catalysts of Example I can be reused with no decrease in activity. This conclusion obviously supports the argument advanced in Example I that the Group IB phthalocyanine catalysts are heterogeneous catalysts for the hydroformylation reaction.

EXAMPLE III

In this example silver phthalocyanine was synthesized and tested as a heterogeneous hydroformylation catalyst in the presence of both a terminal and an internal olefin. The silver phthalocyanine was synthesized by mixing an alcoholic solution of dilithium phthalocyanine and silver nitrate according to the method of P. A. Barret, et al (*J. Chem. Soc.*, 1938, 1157 ff). The deep red lusterous crystals which precipitated were used without further purification.

In this example, 0.10 grams (0.19 mmols) of the silver phthalocyanine and 20 grams of decene-5 (143 mmols) were charged to a glass-lined, stainless-steel, 850 ml rotating autoclave which was equipped with standard external heating and temperature regulating devices. The autoclave was flushed with nitrogen and sealed, subsequently, 21 grams (500 mmols) of liquid propylene was charged by means of a pressurized liquid charging device. The autoclave was then pressurized to 100 atmospheres of carbon monoxide and an additional 100 atmospheres of hydrogen. The autoclave and its contents were heated to 120° C. for a period of time comprising 18 hours and then cooled to room temperature. After the excess gas pressure was carefully vented in a hood and the autoclave was flushed with nitrogen to remove residual carbon monoxide, the liquid products were recovered and analyzed by standard gas-liquid chromatographic techniques. The analysis disclosed that about 2 mmols of the propylene had been converted to butyraldehydes (about 61% normal butyraldehyde) while the decene-5 was recovered unchanged.

The silver phthalocyanine was recovered as an insoluble solid from the product mixture and further experimentation demonstrated that it could be reused with comparable conversions of terminal olefins to aldehydes.

EXAMPLE IV

In this example copper phthalocyanine tetrasulfonate was used as a heterogeneous catalyst dispersed on a sample of α-alumina as a catalyst base. A 50 ml sample of α-alumina spheres was impregnated with 0.30 grams (0.32 mmols) of the copper phthalocyanine tetrasulfonate from an aqueous medium by standard impregnation techniques.

A 20 ml sample of the resultant spheres (0.13 mmols of copper phthalocyanine tetrasulfonate) was charged to the rocking autoclave described in Example I along with 20 grams of heptane as a solvent. The autoclave was sealed and nitrogen flushed as in Example I. Then 21 grams (500 mmols) of propylene was charged as in Example I and the autoclave was pressurized to 160 atmospheres of hydrogen and 40 atmospheres of carbon monoxide. After heating to 120° C. for 18 hours, the liquid product was recovered and analyzed as set forth in Example I above. Said analysis disclosed the presence of about equal molar ratios of iso- and normal-butyraldehydes.

The results of this experiment clearly show that the heterogeneous phthalocyanines can be dispersed on a catalyst base.

EXAMPLE V

In this example 2.2 grams of gold aminophthalocyanine dispersed on 10.5 grams of mordenite, 24.4 grams of hexadecene-1 and 12.0 grams of 2,2,4-trimethylpentane are added to an 850 ml rotating autoclave equipped with external heating and pressurization devices. The autoclave is initially charged with 100 atmospheres of hydrogen and 100 atmospheres of carbon monoxide and maintained at a temperature of 300° C. for a period of time comprising 2.25 hours. The autoclave is carefully purged with nitrogen gas and vented to ambient pressure while the heat is terminated to effect a return to room temperature of the autoclave. The reaction product is recovered and separated from the autoclave and analyzed by means of gas-liquid chromatography. The analysis will disclose the product to be 1-heptadecanol.

EXAMPLE VI

In this example 2.5 grams of copper phthalocyaninecarboxylate dispersed on 10.7 grams of lignite-derived charcoal, 8.4 grams of 2-methylpentene-1 and 15.5 grams of water are charged to a rocking autoclave equipped with external devices for temperature and pressure attainment. The autoclave is rocked for a period of time comprising 6 hours at a temperature of 100° C. and an initial pressure of 100 atmospheres of carbon monoxide and 100 atmospheres of hydrogen. The autoclave is returned to room temperature and pressures by procedures set forth in Example V above. The product was recovered from the autoclave, separated from any unreacted 2-methylpentene-1, water and copper phthalocyanine dispersed lignite charcoal and analyzed by means of gas-liquid chromatography instrumentation, said analysis will disclose the product to be 3-methylhexanol-1.

I claim as my invention:

1. A process for the preparation of a hydroformylation product consisting essentially of alcohols and aldehydes which comprises hydroformylation of a monoolefinic alkene possessing from 3 to 30 carbon atoms with its double bond disposed in the alpha position with carbon monoxide and hydrogen at a temperature of about 15° to about 300° C. and a pressure of from about 1 atmosphere to about 500 atmospheres in the presence of a catalyst system consisting essentially of a Group IB metal phthalocyanine compound and recovering the resultant hydroformylation products.

2. The process of claim 1 further characterized in that the Group IB metal phthalocyanine compound is present in a quantity of from about 0.01 wt. % to about 20.00 wt. %.

3. The process of claim 1 further characterized in that the Group IB metal phthalocyanine compound is copper phthalocyanine.

4. The process of claim 1 further characterized in that the Group IB metal phthalocyanine compound is gold phthalocyanine.

5. The process of claim 1 further characterized in that the Group IB metal phthalocyanine compound is silver phthalocyanine.

6. The process of claim 1 further characterized in that the Group IB metal phthalocyanine compound is dispersed on a solid support.

7. The process of claim 6 further characterized in that the solid support is γ-alumina.

8. The process of claim 6 further characterized in that the solid support is lignite-derived charcoal.

9. The process of claim 6 further characterized in that the solid support is mordenite.

10. The process of claim 1 further characterized in that the alpha olefin is propylene and the resultant hydroformylated product is butyraldehyde.

11. The process of claim 1 further characterized in that the alpha olefin is decene-1 and the resultant hydroformylated product is 1-undecanol.

12. The process of claim 1 further characterized in that the alpha olefin is hexadecene-1 and the resultant hydroformylated product is 1-heptadecanol.

13. The process of claim 1 further characterized in that the alpha olefin is 2-methylpentene-1 and the resultant hydroformylated product is 3-methylhexanol-1.

14. The process of claim 1 further characterized in that the hydroformylation is effected in an inert medium.

15. The process of claim 14 further characterized in that the inert medium is n-pentane.

16. The process of claim 14 further characterized in that the inert medium is 2,2,4-trimethylpentane.

17. The process of claim 14 further characterized in that the inert medium is water.

18. The process of claim 1 further characterized in that the alpha-olefin contains a second internal double bond.

* * * * *